United States Patent
Baynham

(10) Patent No.: US 9,629,727 B2
(45) Date of Patent: Apr. 25, 2017

(54) PEDICLE-BASED CONSTRUCT FACET JOINT FIXATION DEVICE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 14/210,227

(22) Filed: Mar. 13, 2014

(65) Prior Publication Data

US 2014/0277141 A1  Sep. 18, 2014

Related U.S. Application Data

(60) Provisional application No. 61/784,465, filed on Mar. 14, 2013.

(51) Int. Cl.
| | |
|---|---|
| *A61F 2/44* | (2006.01) |
| *A61B 17/70* | (2006.01) |
| *A61F 2/46* | (2006.01) |
| *A61F 2/30* | (2006.01) |

(52) U.S. Cl.
CPC ........ *A61F 2/4405* (2013.01); *A61B 17/7064* (2013.01); *A61F 2/4455* (2013.01); *A61F 2/4611* (2013.01); *A61F 2002/30014* (2013.01); *A61F 2002/30136* (2013.01); *A61F 2002/30281* (2013.01); *A61F 2002/30565* (2013.01); *A61F 2002/30772* (2013.01); *A61F 2002/30785* (2013.01); *A61F 2002/4475* (2013.01)

(58) Field of Classification Search
CPC ..................... A61B 17/7064; A61F 2/4405
See application file for complete search history.

(56) References Cited

U.S. PATENT DOCUMENTS

| | | | |
|---|---|---|---|
| 2010/0191241 A1* | 7/2010 | McCormack et al. | 606/83 |
| 2011/0029085 A1* | 2/2011 | Hynes | A61F 2/447 623/17.16 |

* cited by examiner

*Primary Examiner* — Ellen C Hammond
(74) *Attorney, Agent, or Firm* — McHale & Slavin, P.A.

(57) ABSTRACT

A facet joint fixation device formed from a flexible wedge shaped implant constructed from a single piece of material. The device is defined by an insert end spaced apart from outer end by first and second side members. Each side support is cut by a series of recesses defining a living hinge therebetween.

7 Claims, 3 Drawing Sheets

PEDICLE-BASED CONSTRUCT FACET JOINT FIXATION DEVICE

PRIORITY CLAIM

In accordance with 37 C.F.R. 1.76, a claim of priority is included in an Application Data Sheet filed concurrently herewith. Accordingly, the present application claims the benefit of priority to U.S. provisional patent application Ser. No. 61/784,465 filed on Mar. 14, 2013, entitled "PEDICLE-BASED CONSTRUCT FACET JOINT FIXATION DEVICE", the contents of which are hereby expressly incorporated herein by reference.

FIELD OF THE INVENTION

The present invention relates generally to surgically-implantable spinal devices and, more specifically, to a pedicle-based construct facet joint fixation device.

BACKGROUND OF THE INVENTION

It is often desirable to stabilize/immobilize one or more facet joints of the spine of a patient in the treatment of various spinal ailments/defects. Facet arthrodesis is used to fuse a facet joint including a superior facet and an inferior facet in spinal treatment operations.

There are numerous implants and associated methods for performing stabilization/immobilization. Conventional implants bone screws that are threaded through the superior and inferior facets to immobilize the facet joint so as to permit the adjoined bone sections to fuse together.

SUMMARY OF THE INVENTION

Embodiments of the invention are directed, inter alia, to a facet joint fixation device that consists of a flexible wedge shaped implant that can provide anchoring for a pedicle screw implant. The facet fixation device is preferably constructed from a single piece of material having an insert end spaced apart from outer end by first and second arcuate side members. Each side support is cut by a series of recesses defining a living hinge therebetween. Each member is capable of being bent back and forth due to the retained thickness which provides a spring hinge type resilience.

Upon insertion, a pedicle screw can be implanted and positioned between the members and the insert end. The flexible members allows a surgeon to gain access from unobstructed angles. The flexible members serve as a guide for ideal placement of a pedicle screw and dramatically increase the resistance to pedicle screw pullout.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 2:
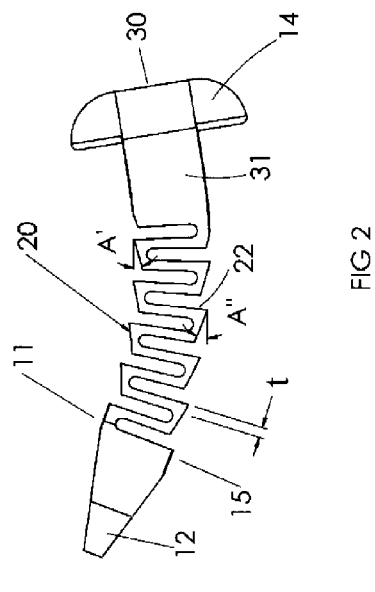
FIG. 2 is a schematic representation of an embodiment of the device showing a side view of a flexing device.
Figure 4:
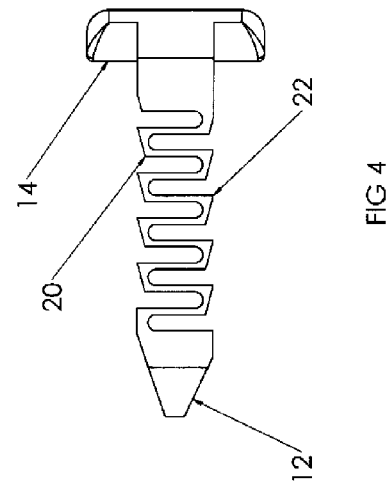
FIG. 4 is a schematic representation of an embodiment of the device showing various embodiments of the structures.
Figure 1:
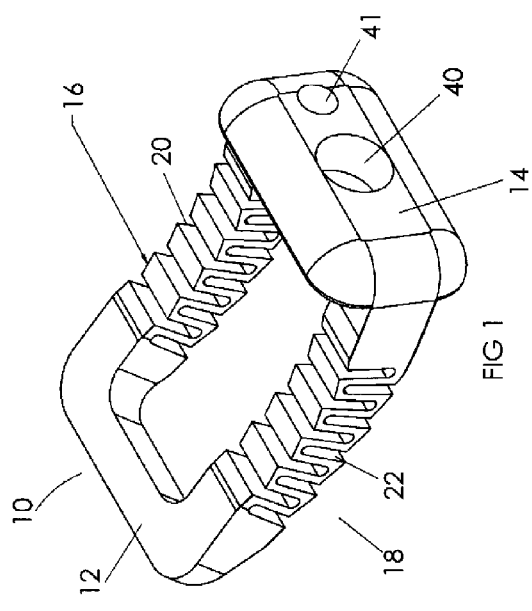
FIG. 1 is a schematic representation of an embodiment of the device showing a three-dimensional view of the device when the side members are flexed after insertion.
Figure 3:
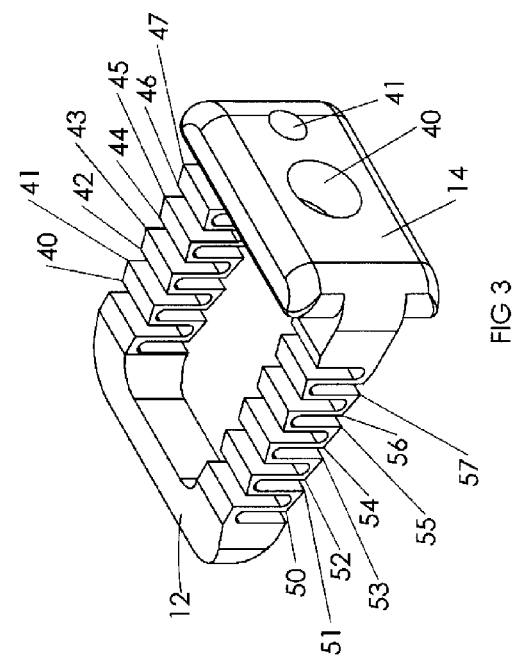
FIG. 3 is a schematic representation of an embodiment of the device showing a three-dimensional view of the device prior to insertion wherein the side members are not flexed.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within or more than 1 standard deviation, per the practice in the art. Alternatively, "about" can mean a range of up to 20%, preferably up to 10%, more preferably up to 5%, and more preferably still up to 1% of a given value. Alternatively, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The following description of the preferred embodiments is merely exemplary in nature and is in no way intended to limit the invention, its application or uses.

Referring now to the Figures in general, disclosed is a facet joint fixation device that consists of a flexible wedge shaped implant 10 that can provide anchoring for a pedicle screw implant. The facet fixation device is preferably constructed from a single piece of biocompatible materials, such as titanium, or any conventional material used for surgical implants, such as stainless steel and its many different alloys, titanium alloys, metallic alloys, polymeric materials, plastics, plastic composites, ceramic and any other metal or material with the requisite strength and biologically inert properties. However, it is to be understood, that the various parts of the device may be constructed from various materials in some embodiments. For example, the side members may be made from a material that provides the requisite strength but also flexibility, whereas the insert end and spacer end are made from a rigid material that can be subjected to force without bending or buckling. If desired, the insert end and/or the side members can be coated with a lubricant or material that provides a lubricating effect. In some embodiments, the insert end and/or the spacer end may comprise one or more layers of materials, such as, for example, plastic, polymers, metals or any other biocompatible conventional material(s). In other embodiments, the device may be coated with a biocompatible material, for example, medical grade thermoplastic elastomeric compounds.

The flexible wedge shaped implant 10 is defined by an insert end 12 spaced apart from an outer or spacer end 14 by a first 16 and second 18 side members. Each side member is cut by a series of recesses 20 and 22 defining a living hinge between the insert end 12 and the outer end 14. The first 16 and second 18 side member forming the living hinge structure has a thickness "t" and are formed from a continuous piece of material having a first side surface with the first series of recesses 20 extending therefrom and perpendicular thereto. The second series of recesses 22 extend from a second side surface 15 and positioned adjacent to the first series of recesses 20. In addition, the recesses serve the purpose of stabilizing or provide grip to prevent slippage or movement of the device by including a slope angle A' on the first side surface and angle A" on the second side surface. The first side surface 11 allows ease of insertion between bone with lower edges 40, 42, 44, and 46 sloped toward raised edges 41, 43, 45 and 47 respectfully, of the first side surface 11 to inhibit removal after installation. Similarly, side surface 15 allows ease of insertion between bone with lower edges 50, 52, 54 and 56 sloped toward raised edges 51, 53, 55 and 57 of the second side surface 15 to inhibit removal after installation. Each side member 16 and 18 is capable of being bent back and forth due to the retained thickness which provide spring hinge type resilience. In preferred embodiments, the side members can flex at least about 20° relative to a horizontal axis, preferably about 45° relative to a horizontal axis, preferably about 50° relative to a horizontal axis, preferably about 75° relative to a horizontal axis, preferably 90° relative to a horizontal axis, preferably about 180° relative to a horizontal axis. In some embodiments, the flexibility is about 270° relative to a horizontal axis.

Figure 6:
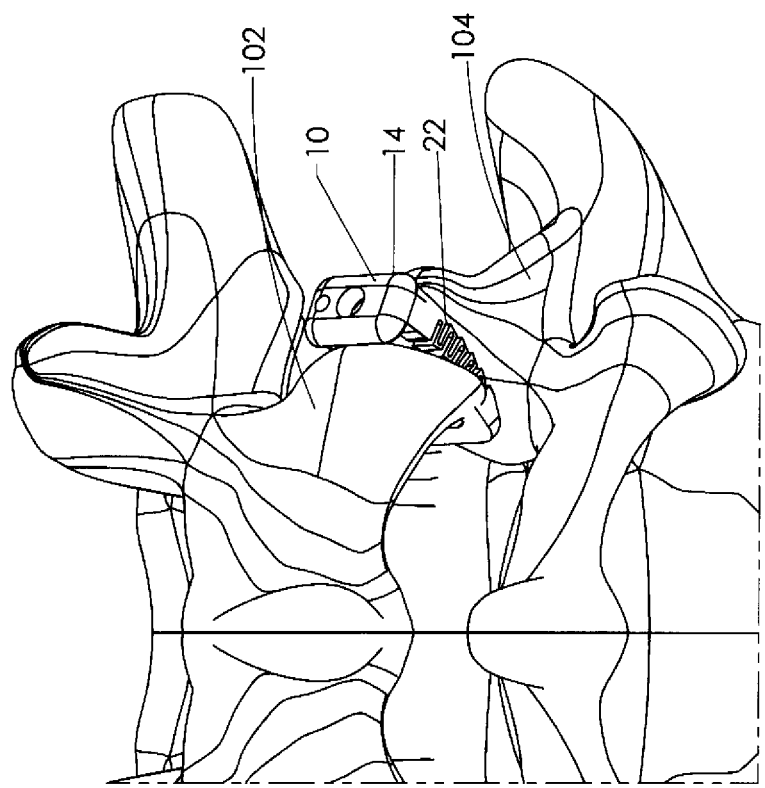
FIG. 6 is a schematic representation showing the device inserted between adjacent vertebrae.
Figure 5:
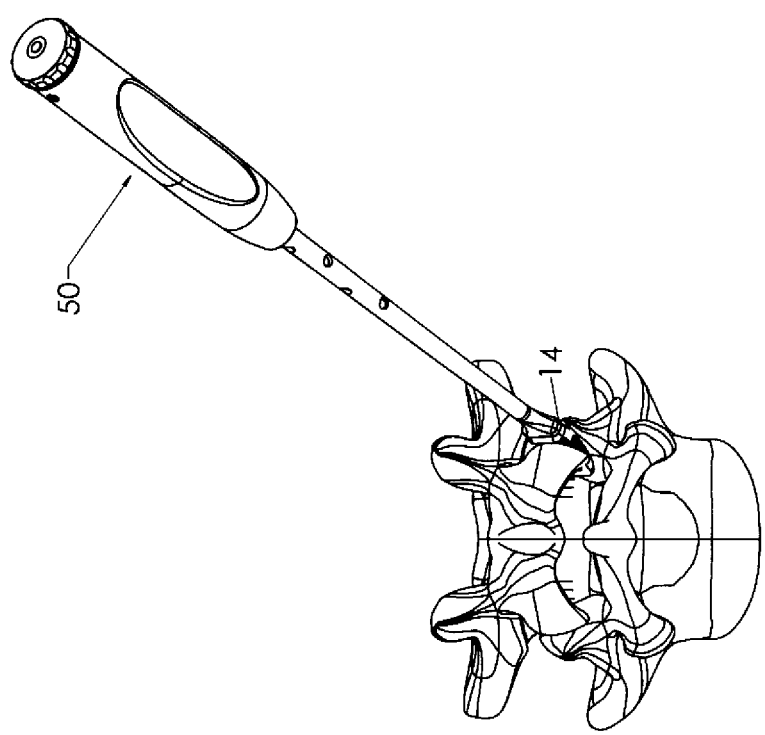
FIG. 5 is a schematic representation showing the vertebrae and the spacer inserter used for inserting the device.
Figure 7:
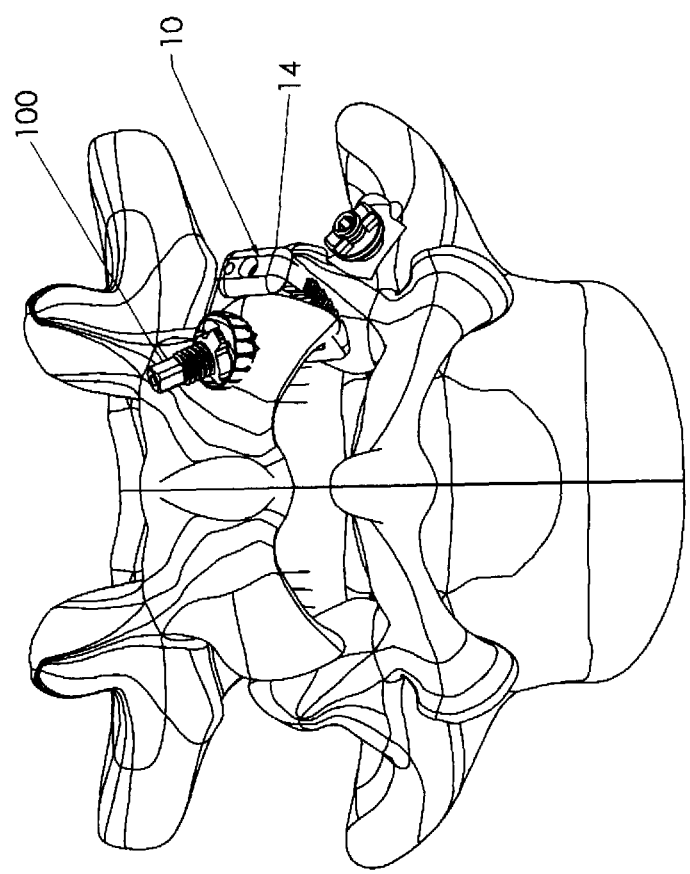
FIG. 7 is a schematic representation showing the inserted device and a pedicle anchor.

Referring in particular to FIGS. 5-7, a spacer inserter 50 attaches to the flexible wedge shaped implant 10 to permit ease of insertion between the facets 102 and 104. Upon insertion, a pedicle screw 100 can be implanted and positioned between the arcuate side members 16 and 18 and the insert end 12. The flexible arcuate side members 16 and 18 allow a surgeon to gain access from unobstructed angles as illustrated by the curvature of the implant. The flexible side members 16 and 18 further serve as a guide for ideal placement of a pedicle screw 100 and dramatically increases the resistance to pedicle screw 100 pullout.

Accordingly, in preferred embodiments, a facet spacer device comprises an insert end, a spacer end, wherein the insert end and the spacer end are connected by a first and a second side member, wherein each side member comprises at least one recess defining a hinge structure. In a preferred embodiment, the side members comprise a plurality of recesses defining a hinge structure.

In a preferred embodiment, the insert end comprises a tapered end and the spacer end comprises a curved surface or a planar surface having flat or curved sides or combinations thereof, and at least one opening 40, 41 for receiving a pedicle screw or other instruments.

In preferred embodiments, the spacer end is wider than the height of the side members. The side members connecting the insert end and the spacer end are attached to the spacer end, in a position equidistant from each end of the planar or curved surface. Accordingly, the height of the spacer end 30 is greater than the height of the side members 31 by at least about 0.1 fold to about 10 fold.

Embodiments are also directed to methods and procedures for using the device. In a preferred embodiment, a method of implanting a pedicle screw in a patient in need thereof, comprises inserting a flexible wedge-shaped implant between adjacent vertebrae, the flexible wedge-shaped implant comprising an insert end, an outer end, wherein the insert end and the outer end are spaced apart by a first and a second side member, each side member having one or more recesses defining a hinge structure and providing flexibility. The insert end comprises a tapered end for ease of inserting the device in between adjacent vertebrae.

In preferred embodiments, the outer end comprises a planar surface having flat or curved sides or combinations thereof, and at least one opening for receiving the pedicle screw. It is to be understood that the openings may vary in size for receiving various surgical or other instruments.

In embodiments, the recesses defining the hinge structure further provide an anchoring thereby preventing the device from moving during the procedure or pedicle screw pullout.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A flexible wedge shaped implant comprising an insert end spaced apart from a spacer end by a first and a second side member forming a living hinge structure having a thickness, said first and second side member each formed from a continuous piece of material having a first side surface with a first series of recesses extending therefrom and perpendicular thereto with said first side surface having a slope between adjacent recesses, and a second series of recesses extending from a second side surface positioned adjacent said first series of recesses with said second side surface having a slope between adjacent recesses; said thickness of each said side member is uniform between said first and second side surface; said spacer end including an opening for receipt of a pedicle screw; whereby said insert end can be offset from said outer end by the flex of said living hinge structure and said thickness of said living hinge structure remains uniform throughout the offset.

2. The flexible wedge-shaped implant of claim 1, wherein the insert end comprises a tapered end.

3. The flexible wedge-shaped implant of claim 1, wherein the outer end comprises a planar surface having flat or curved sides or combinations thereof, and at least one opening for receiving a surgical instrument.

4. The flexible wedge-shaped implant of claim 1, wherein the outer end comprises a curved surface and at least one opening for receiving a surgical instrument.

5. A flexible wedge shaped implant comprising an insert end spaced apart from a spacer end by a first and a second side member forming a living hinge structure having a thickness, said first and second side member each formed from a continuous piece of material having a first side surface with a first series of recesses extending therefrom and perpendicular thereto with said first side surface having a slope between adjacent recesses, and a second series of recesses extending from a second side surface positioned adjacent said first series of recesses forming an arcuate profile with said second side surface having a slope between adjacent recesses; said thickness of each said side member is uniform between said first and second side surface; said spacer end including an opening for receipt of a pedicle screw; whereby said insert end can be offset from said outer end by the flex of said living hinge structure and said thickness of said living hinge structure remains uniform throughout the offset.

6. The facet spacer device of claim 5, wherein the spacer end is wider than the height of the side members by at least about 0.1 fold to about 10 fold.

7. The facet spacer device of claim 5, wherein the insert end and the spacer end are rigid.

* * * * *